United States Patent
Shibata

(10) Patent No.: US 10,835,200 B2
(45) Date of Patent: Nov. 17, 2020

(54) ULTRASOUND DIAGNOSIS APPARATUS

(71) Applicant: Toshiba Medical Systems Corporation, Otawara (JP)

(72) Inventor: Chihiro Shibata, Nasushiobara (JP)

(73) Assignee: Canon Medical Systems Corporation, Otawara (JP)

(*) Notice: Subject to any disclaimer, the term of this patent is extended or adjusted under 35 U.S.C. 154(b) by 581 days.

(21) Appl. No.: 15/232,308

(22) Filed: Aug. 9, 2016

(65) Prior Publication Data

US 2017/0071567 A1    Mar. 16, 2017

(30) Foreign Application Priority Data

Sep. 16, 2015   (JP) ................ 2015-182593

(51) Int. Cl.
  *A61B 8/06*   (2006.01)
  *A61B 8/08*   (2006.01)
  *A61B 8/00*   (2006.01)

(52) U.S. Cl.
  CPC ............. *A61B 8/06* (2013.01); *A61B 8/469* (2013.01); *A61B 8/488* (2013.01); *A61B 8/54* (2013.01);
  (Continued)

(58) Field of Classification Search
  CPC .......... A61B 8/06; A61B 8/469; A61B 8/483; A61B 8/488; A61B 8/5223; A61B 8/54; A61B 8/58
  See application file for complete search history.

(56) References Cited

U.S. PATENT DOCUMENTS 5,891,040 A * 4/1999 Grenon .............. G01S 15/8979
                                              600/453
8,157,734 B2 * 4/2012 Nakata ..................... A61B 8/06
                                              600/437
(Continued)

FOREIGN PATENT DOCUMENTS

JP    2014-42823    3/2014
JP    2014-158698   9/2014

OTHER PUBLICATIONS

Aleksandr Rovner, The principle of ultrasound, Sep. 7, 2015, ECHOpedia, Pertinent p. 4 (Year: 2015).*

(Continued)

*Primary Examiner* — Katherine L Fernandez
(74) *Attorney, Agent, or Firm* — Oblon, McClelland, Maier & Neustadt, L.L.P.

(57) ABSTRACT

An ultrasound diagnosis apparatus according to an embodiment includes Doppler processing circuitry and processing circuitry. The Doppler processing circuitry filters a data sequence of reflected-wave data at the same positions across a plurality of frames in a frame direction to collect blood flow information in a predetermined region of interest. The processing circuitry receives a first instruction to change the range of flow rate values to be displayed, in display of the blood flow information. The processing circuitry receives a second instruction to change a setting related to the region of interest. The processing circuitry changes the range of flow rate values in response to the first instruction when receiving the first instruction, and performs an adjustment for maintaining the range of flow rate values when receiving the second instruction.

7 Claims, 10 Drawing Sheets

(52) U.S. Cl.
CPC ............... *A61B 8/465* (2013.01); *A61B 8/483* (2013.01); *A61B 8/5223* (2013.01)

(56) References Cited

U.S. PATENT DOCUMENTS

| | | | | |
|---|---|---|---|---|
| 2003/0018264 A1* | 1/2003 | Suzuki | ............. | A61B 8/06 600/453 |
| 2005/0228280 A1* | 10/2005 | Ustuner | ............. | A61B 8/06 600/443 |
| 2006/0052698 A1* | 3/2006 | Loupas | ............. | A61B 8/06 600/437 |
| 2008/0015440 A1* | 1/2008 | Shandas | ............. | A61B 8/06 600/458 |
| 2009/0088641 A1* | 4/2009 | Baba | ............. | A61B 8/06 600/455 |
| 2013/0225986 A1* | 8/2013 | Eggers | ............. | A61B 8/0825 600/425 |
| 2014/0039317 A1 | 2/2014 | Sato | | |
| 2015/0320395 A1 | 11/2015 | Sato | | |
| 2015/0374337 A1* | 12/2015 | Nishihara | ............. | A61B 8/463 600/443 |

OTHER PUBLICATIONS

Frequency and Period of a Wave, Sep. 15, 2015, the Physics Classroom, Pertinent p. 1 (Year: 2015).*

How ultrasound imaging works explained simply, May 6, 2015, how equipment works, Pertinent p. 23 (Year: 2015).*

* cited by examiner

FIG.5
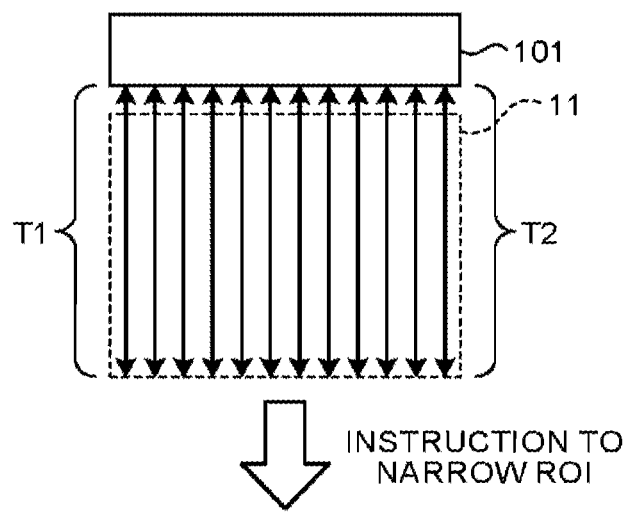
INSTRUCTION TO NARROW ROI
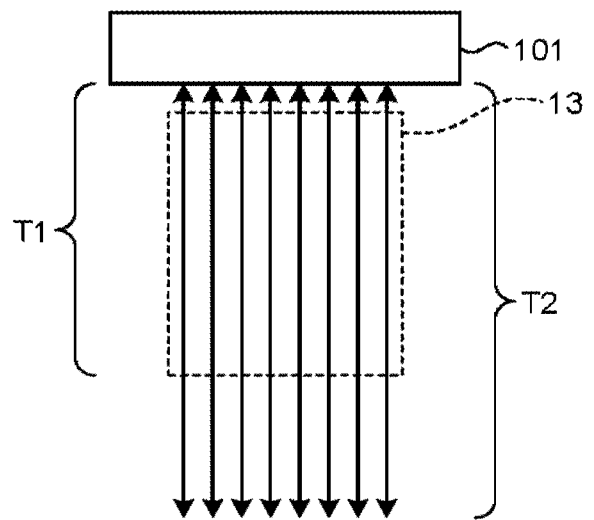

ULTRASOUND DIAGNOSIS APPARATUS

CROSS-REFERENCE TO RELATED APPLICATIONS

This application is based upon and claims the benefit of priority from Japanese Patent Application No. 2015-182593, filed on Sep. 16, 2015; the entire contents of which are incorporated herein by reference.

FIELD

Embodiments relate to ultrasound diagnosis apparatuses.

BACKGROUND

Conventional ultrasound diagnosis apparatuses have a function for generating and displaying blood flow information from reflected waves of ultrasound using a Doppler method based on the Doppler effect. There has been proposed a technique for obtaining blood flow information in which clutter components from tissue having low movement speed is significantly reduced, compared with the ordinary Doppler method, by imaging blood flow at high speed, high resolution, and high frame rate.

BRIEF DESCRIPTION OF THE DRAWINGS

FIG. 5 is a view illustrating the process of the adjusting function according to the first embodiment;

DETAILED DESCRIPTION

An ultrasound diagnosis apparatus according to an embodiment includes Doppler processing circuitry and processing circuitry. The Doppler processing circuitry filters a data sequence of reflected-wave data at the same positions across a plurality of frames in a frame direction to collect blood flow information in a predetermined region of interest. The processing circuitry receives a first instruction to change a range of flow rate values to be displayed, in display of the blood flow information. The processing circuitry receives a second instruction to change a setting related to the region of interest. The processing circuitry changes the range of flow rate values in response to the first instruction when receiving the first instruction, and performs an adjustment for maintaining the range of flow rate values when receiving the second instruction.

With reference to the accompanying drawings, the ultrasound diagnosis apparatus according to an embodiment will be now described.

First Embodiment

Figure 1:
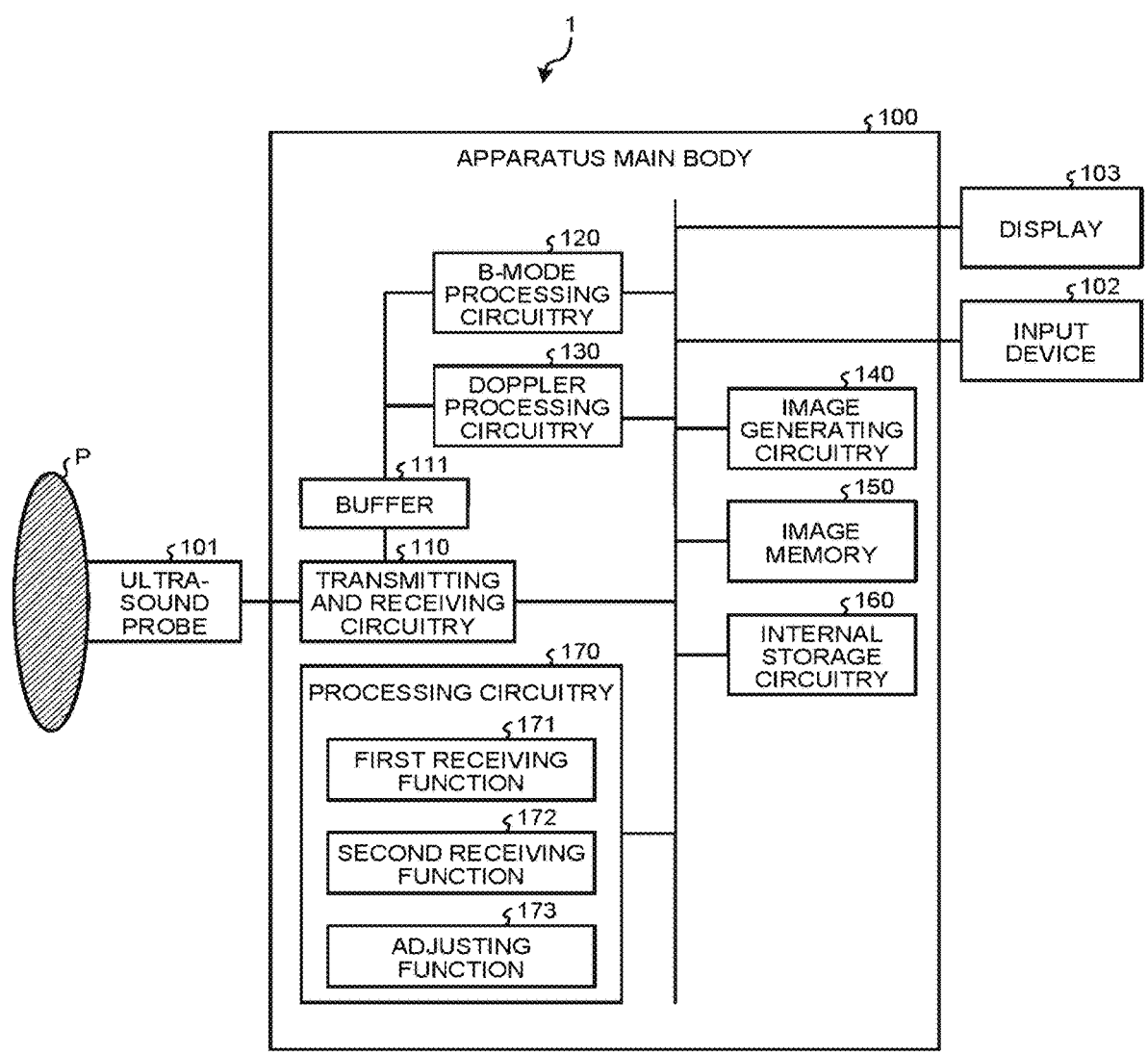
FIG. 1 is a block diagram illustrating an example configuration of an ultrasound diagnosis apparatus according to a first embodiment.

FIG. 1 is a block diagram illustrating an example configuration of an ultrasound diagnosis apparatus 1 according to a first embodiment. As illustrated in FIG. 1, the ultrasound diagnosis apparatus 1 according to the first embodiment includes an ultrasound probe 101, an input device 102, a display 103, and an apparatus main body 100. The ultrasound probe 101, the input device 102 and the display 103 are communicatively coupled to the apparatus main body 100. A subject P is not included in the configuration of the ultrasound diagnosis apparatus 1.

The ultrasound probe 101 performs ultrasound transmission and reception. The ultrasound probe 101 includes a plurality of piezoelectric transducer elements, for example. The piezoelectric transducer elements generate ultrasound raised on driving signals supplied by a transmitting and receiving circuitry 110 described below, which is included in the apparatus main body 100. The piezoelectric transducer elements of the ultrasound probe 101 receive reflected waves from the subject P to convert them into electrical signals. The ultrasound probe 101 further includes a matching layer provided to the piezoelectric transducer elements and a backing member that prevents ultrasound from propagating rearward from the piezoelectric transducer elements. The ultrasound probe 101 is detachably coupled to the apparatus main body 100.

When the ultrasound is transmitted from the ultrasound probe 101 to the subject P, the transmitted ultrasound is repeatedly reflected on surfaces of discontinuity of acoustic impedances at tissue in the body of subject P and is received as reflected-wave signals by the piezoelectric transducer elements of the ultrasound probe 101. The amplitude of the received reflected-wave signal is dependent on the difference between the acoustic impedances on the surface of discontinuity on which the ultrasound is reflected. When a transmitted ultrasound pulse is reflected on the surface of a moving blood flow, a moving cardiac wall, and any other moving object, due to the Doppler effect, the frequency of the reflected-wave signal is shifted depending on the velocity component of the moving object in an ultrasound transmission direction.

The ultrasound probe 101 according to the first embodiment is applicable to 1D array probes that scan the subject P two-dimensionally, or mechanical 4D probes and 2D array probes that scan the subject P three-dimensionally.

The input device 102 corresponds to a device, such as a mouse, a keyboard, a button, a panel switch, a touch command screen, a foot switch, a trackball, and a joystick. The input device 102 receives various types of setting requests from an operator of the ultrasound diagnosis apparatus 1 and transfers the received various types of setting requests to the apparatus main body 100.

The display 103 displays a graphical user interface (GUI) that allows the operator of the ultrasound diagnosis apparatus 1 to input various kinds of setting requests with the input device 102, and displays ultrasound image data generated in the apparatus main body 100 and any other data.

The apparatus main body 100 is an apparatus that generates ultrasound image data based on the reflected-wave signals received by the ultrasound probe 101. The ultrasound image data generated by the apparatus main body 100 illustrated in FIG. 1 may be two-dimensional ultrasound image data generated based on two-dimensional reflected-wave signals, or may be three-dimensional ultrasound image data generated based on three-dimensional reflected-wave signals.

As illustrated in FIG. 1, the apparatus main body 100 includes the transmitting and receiving circuitry 110, a B-mode processing circuitry 120, Doppler processing circuitry 130, image generating circuitry 140, an image memory 150, internal storage circuitry 160, and processing circuitry 170. The transmitting and receiving circuitry 110, the B-mode processing circuitry 120, the Doppler processing circuitry 130, the image generating circuitry 140, the image memory 150 the internal storage circuitry 160, and the processing circuitry 170 are communicatively coupled to each other.

The transmitting and receiving circuitry 110 controls the ultrasound transmission and reception performed by the ultrasound probe 101, based on instructions from the processing circuitry 170 as described below. The transmitting and receiving circuitry 110 includes a pulse generator, a transmission-delaying circuit, and a pulser, and supplies driving signals to the ultrasound probe 101. The pulse generator repeatedly generates rate pulses for forming transmitted ultrasound at a predetermined pulse repetition frequency (PRF). Furthermore, the transmission-delaying circuit gives a delay time for each piezoelectric transducer element to the corresponding rate pulse generated by the pulse generator. Such a delay time is required to converge the ultrasound generated by the ultrasound probe 101 into a beam and determine transmission directionality. Furthermore, the pulser applies the driving signals (driving pulses) to the ultrasound probe 101 at a timing based on the rate pulses. That is, the transmission-delaying circuit desirably adjusts the transmission direction of the ultrasound transmitted from the surface of the piezoelectric transducer elements, by varying the delay time given to each rate pulse.

The transmitting and receiving circuitry 110 has a function to be able to instantly change, for example, a transmission frequency and a transmission driving voltage, to perform a predetermined scanning sequence based on instructions from the processing circuitry 170 as described below. In particular, one change in the transmission driving voltage is achieved by a linear-amplifier-type oscillation circuit that is capable of instantly switching the value of the voltage, or by a mechanism that electrically switches a plurality of power sources.

Furthermore, the transmitting and receiving circuitry 110 includes an amplifying circuit, an analog to digital (A/D) converter, a reception-delaying circuit, an adder, a quadrature-detection circuit, and generates reflected-wave data by performing various types of processing on the reflected-wave signal received by the ultrasound probe 101. The amplifying circuit performs gain-correction processing by amplifying the reflected-wave signal for each channel. The A/D converter performs A/D conversion of the gain-corrected reflected-wave signal. The reception-delaying circuit gives a reception delay signal required to determine the reception directionality to the digital data. The adder performs adding processing on the reflected-wave signal to which the reception delay time has been given by the reception-delaying circuit. The adding processing performed by the adder enhances a reflected component from the direction corresponding to the reception directivity of the reflected wave signal.

The quadrature-detection circuit converts an output signal from the adder into an in-phase signal (I signal) and a quadrature-phase signal (Q signal) in a baseband. Furthermore, as the reflected-wave data, the quadrature-detection circuit stores the I signal and the Q signal (hereinafter referred to as an "IQ signal") into a buffer 111. The quadrature-detection circuit may store the output signal from the adder into the buffer 111 after converting the signal into a radio frequency (RF) signal. The IQ signal and the RF signal are signals (received signals) that contain phase information. Hereinafter, the reflected-wave data output from the transmitting and receiving circuitry 110 may be referred to as a received signal.

The buffer 111 is a buffer that temporarily stores therein the reflected-wave data (IQ signal) generated by the transmitting and receiving circuitry 110. Specifically, the buffer 111 stores therein several frames of IQ signals or several volumes of IQ signals. For instance, the buffer 111 is a first-in first-out (FIFO) memory and stores therein predetermined frames of IQ signals. For instance, when a frame of IQ signals is newly generated by the transmitting and receiving circuitry 110, the buffer 111 drops a frame of IQ signals having the oldest generation time, and stores therein the newly generated frame of IQ signals. The buffer 111 is communicatively coupled to each of the transmitting and receiving circuitry 110, the B-mode processing circuitry 120, and the Doppler processing circuitry 130.

The transmitting and receiving circuitry 110 can generate the reflected-wave data having a plurality of reception focuses using the reflected-wave signals from the piezoelectric transducer elements obtained by one transmission of an ultrasound beam. That is, the transmitting and receiving circuitry 110 can perform parallel simultaneous reception processing. The first embodiment is applicable even if the transmitting and receiving circuitry 110 fails to implement the parallel simultaneous reception processing.

The B-mode processing circuitry 120 and the Doppler processing circuitry 130 are signal processing units that perform various types of signal processing on the reflected-wave data that the transmitting and receiving circuitry 110 generates from the reflected-wave signal. The B-mode processing circuitry 120 performs logarithmic amplification, envelope detection processing, logarithmic compression, and other processing on the reflected-wave data (IQ signal) read from the buffer 111, and generates data (B-mode data) in which the signal intensity of many points is represented by the brightness of luminance.

The B-mode processing circuitry 120 can change a frequency band to be imaged by varying a detection frequency through filtering. The filtering function of the B-mode processing circuitry 120 can be used to perform harmonic imaging, such as contrast harmonic imaging (CHI) and tissue harmonic imaging (THI).

Furthermore, the ultrasound diagnosis apparatus 1 according to the first embodiment can perform the THI by using the filtering function of the B-mode processing circuitry 120.

In performing the harmonic imaging, such as the CHI and the THI, the B-mode processing circuitry 120 can also extract harmonic components by a method different from the filtering described above. The harmonic imaging performs an imaging method. Such an imaging method includes an amplitude modulation (AM) method, a phase modulation (PM) method, and an AMPM method that combines the AM method with the PM method. The AM method, the PM method, and the AMPM method perform ultrasound transmission multiple times for the same scanning line with different amplitudes and phases. This causes the transmitting and receiving circuitry 110 to generate and output a plurality of pieces of reflected-wave data (received signals) for each scanning line. Subsequently, the B-mode processing circuitry 120 performs adding and subtracting of the pieces of reflected-wave data (received signals) for each scanning line according to a modulation method, to extract the harmonic components. The B-mode processing circuitry 120 then performs envelope detection processing and other processing on the harmonic components of the reflected-wave data (received signals) to generate the B-mode data. The Doppler processing circuitry 130 performs frequency analysis on the reflected-wave data read from the buffer 111, to thereby generate data (Doppler data) in which motion information on a moving body within a scanning range based on the Doppler effect is extracted. Specifically, the Doppler processing circuitry 130 generates Doppler data in which an average velocity, an average variance, an average power value, and any other parameter are estimated at each of a plurality of sample points as motion information on a moving body. The moving body as used herein refers to, for example, a blood flow, a tissue such as the wall of the heart, and a contrast agent. The Doppler processing circuitry 130 according to the present embodiment generates Doppler data in which an average velocity of the blood flow, an average variance of the blood flow, an average power value of the blood flow, and any other parameter are estimated at each of a plurality of sample points as motion information on the blood flow (blood flow information).

The ultrasound diagnosis apparatus 1 according to the present embodiment can perform a color Doppler method, which is also referred to as a color flow mapping (CFM) method, by using the function of the Doppler processing circuitry 130 described above. The CFM method performs the ultrasound transmission and reception multiple times on a plurality of scanning lines. Subsequently, the CFM method performs moving-target-indicator (MTI) filtering on a data sequence at the same positions to reduce a signal (a clutter signal) from non-moving tissue or tissue having low movement speed to extract a signal from blood flow. From this blood signal, the CFM method estimates blood flow information, including the rate of the blood flow, the dispersion of the blood flow, and the power of the blood flow. The image generating circuitry 140 described below generates ultrasound image data (color Doppler image data) in which the distribution of the estimated result is displayed, for example, two-dimensionally and in color. Subsequently, the display 103 displays the color Doppler image data. The Doppler processing circuitry 130 is an example of a collection unit that collects blood flow information. The Doppler processing circuitry 130 as the collection unit filters a data sequence of reflected-wave data at the same positions across a plurality of frames in the frame direction to collect the blood flow information in a predetermined region of interest.

Typical examples of the MTI filter include filters having constant coefficients such as an infinite impulse response (IIR) filter having Butterworth characteristics and a polynomial regression filter (PRF). In contrast, the Doppler processing circuitry 130 according to the present embodiment uses an adaptive MTI filter that changes coefficients in response to an input signal as the MTI filter. Specifically, the Doppler processing circuitry 130 according to the present embodiment uses a filter known as an "eigenvector regression filter" as the adaptive MTI filter. Hereinafter, the "eigenvector regression filter", which is the adaptive MTI filter using eigenvectors, is referred to as an "eigenvector MTI filter".

The eigenvector MTI filter calculates eigenvectors from a correlation matrix, and calculates coefficients used for reducing clutter components from the calculated eigenvectors. This method is an application of methods used in principal component analysis, Karhunen-Loeve transform, and an eigenspace method.

The Doppler processing circuitry 130 using the eigenvector MTI filter according to the first embodiment calculates the correlation matrix of a scanning range from a data sequence of successive reflected-wave data at the same positions (the same sampling points). For instance, the Doppler processing circuitry 130 calculates eigenvalues of the correlation matrix and an eigenvector corresponding to each eigenvalue. The Doppler processing circuitry 130 then calculates, for example, a matrix having a reduced rank in which each eigenvector is aligned based on the magnitude of each eigenvalue. This calculated matrix is a filter matrix for reducing clutter components. The Doppler processing circuitry 130 determines the number of principal components to be reduced, i.e., the value of a rank cut-off number, using a predetermined value or a value instructed by the operator, for example. However, if the scanning range includes tissue having moving speed that varies with time due to pulsation, such as a heart and a blood vessel, it is suitable that the value of the rank cut-off number is adaptively determined from the magnitude of the eigenvalues. That is, the Doppler processing circuitry 130 changes the number of principal components to be reduced, depending on the magnitude of the eigenvalues of the correlation matrix. In the present embodiment, the Doppler processing circuitry 130 changes the rank number to be reduced, depending on the magnitude of the eigenvalues.

The Doppler processing circuitry 130 uses a filter matrix to output a data sequence in which clutter components are reduced and a blood flow signal derived from the blood flow is extracted from a data sequence of successive reflected-wave data at the same positions (same sample points). The Doppler processing circuitry 130 estimates blood flow information by performing self-correlation calculation using the data and any other calculation, and outputs the estimated blood flow information.

The image generating circuitry 140 generates the ultrasound image data from the data generated by the B-mode processing circuitry 120 and the Doppler processing circuitry 130. The image generating circuitry 140 generates two-dimensional B-mode image data representing the intensity of reflected waves as luminance from two-dimensional B-mode data generated by the B-mode processing circuitry 120. Furthermore, the image generating circuitry 140 generates two-dimensional Doppler image data that images blood flow information from two-dimensional Doppler data generated by the Doppler processing circuitry 130. The two-dimensional Doppler image data is rate-image data, dispersion-image data, power-image data, or a combination of these. As the Doppler image data, the image generating circuitry 140 generates color Doppler image data in which blood flow information is displayed in color, or generates Doppler image data in which a piece of blood flow information is displayed in grayscale.

The image generating circuitry 140 typically converts (performs scan conversion) a scanning-line signal sequence from an ultrasound scan into a scanning-line signal sequence in a video format typified by, for example, television and generates ultrasound image data for display. Specifically, the image generating circuitry 140 generates the ultrasound image data for display by performing coordinate transformation according to an ultrasound scanning mode used by the ultrasound probe 101. Furthermore, in addition to the scan conversion, the image generating circuitry 140 performs various types of image processing, for example, using a plurality of image frames after the scan conversion. Examples of such image processing include image processing (smoothing processing) that regenerates an average image of brightness, and image processing (edge enhancement processing) that uses a differential filter within an image. In addition, the image generating circuitry 140 combines the ultrasound image data with text information on various parameters, scales, and body marks, for example.

That is, the B-mode data and the Doppler data are ultrasound image data before the scan conversion processing, whereas data generated by the image generating circuitry 140 is ultrasound image data for display after the scan conversion processing. The B-mode data and the Doppler data are also referred to as "raw data". The image generating circuitry 140 generates the two-dimensional ultrasound image data for display from the two-dimensional ultrasound image data before the scan conversion processing.

Furthermore, the image generating circuitry 140 generates three-dimensional B-mode image data for display by performing coordinate transformation on three-dimensional B-mode data generated by the B-mode processing circuitry 120. In addition, the image generating circuitry 140 generates three-dimensional Doppler image data by performing coordinate transformation on three-dimensional Doppler data generated by the Doppler processing circuitry 130.

Furthermore, the image generating circuitry 140 performs rendering processing on volume data, to generate various types of two-dimensional image data for displaying the volume data on the display 103. An example of the rendering processing performed by the image generating circuitry 140 is processing that generates multi planar reconstruction (MPR) image data from the volume data by implementing an MPR method. Another example of the rendering processing performed by the image generating circuitry 140 is volume rendering (VR) processing that generates two-dimensional image data reflecting three-dimensional information.

The image memory 150 is a memory that stores therein the image data for display generated by the image generating circuitry 140. Furthermore, the image memory 150 can store therein the data generated by the B-mode processing circuitry 120 and the Doppler processing circuitry 130. After a diagnosis, the operator can retrieve the B-mode data and the Doppler data stored in the image memory 150, for example. The retrieved data passes through the image generating circuitry 140 to serve as the ultrasound image data for display. The image memory 150 can also store therein the reflected-wave data output from the transmitting and receiving circuitry 110.

The internal storage circuitry 160 stores therein control programs for performing the ultrasound transmission and reception, image processing, and display processing, as well as storing therein various types of data, such as diagnosis information (e.g., patient IDs, medical doctor's observations), diagnosis protocols, and various types of body marks. Furthermore, if needed, the internal storage circuitry 160 is used for storing therein, for example, the image data stored in the image memory 150. The data stored in the internal storage circuitry 160 can be also transferred into an external apparatus via an interface (not illustrated). The internal storage circuitry 160 can also store therein data transferred from the external apparatus via the interface (not illustrated).

The processing circuitry 170 controls the overall processing performed by the ultrasound diagnosis apparatus 1. Specifically, the processing circuitry 170 controls the processing performed by the transmitting and receiving circuitry 110, the B-mode processing circuitry 120, the Doppler processing circuitry 130, and the image generating circuitry 140, based on various types of setting requests input by the operator via the input device 102 as well as various types of control programs and various types of data read from the internal storage circuitry 160. Furthermore, the processing circuitry 170 performs the control so that the display 103 displays the ultrasound image data for display stored in the image memory 150 and the internal storage circuitry 160.

For instance, the processing circuitry 170 controls ultrasound scanning by controlling the ultrasound probe 101 via the transmitting and receiving circuitry 110. The CFM method typically displays the color Doppler image data and the B-mode image data. The color Doppler image data is blood image data, and the B-mode image data is tissue image data. To display these types of data, the processing circuitry 170 causes the ultrasound probe 101 to perform a first ultrasound scan, to obtain blood flow information in a first scanning range. For instance, the first ultrasound scan is an ultrasound scan for collecting the color Doppler image data in the Doppler mode. Furthermore, in addition to the first ultrasound scan, the processing circuitry 170 causes the ultrasound probe 101 to perform a second ultrasound scan to obtain tissue shape information in a second scanning range. For instance, the second ultrasound scan is an ultrasound scan for collecting the B-mode image data in the B-mode.

Furthermore, the processing circuitry 170 performs a first receiving function 171, a second receiving function 172, and an adjusting function 173. The processing functions performed by the first receiving function 171, the second receiving function 172 and the adjusting function 173, which are components of the processing circuitry 170, are stored in the internal storage circuitry 160, for example, in the form of computer programs executable by a computer. The processing circuitry 170 is a processor that implements the function corresponding to each computer program by reading the program from the internal storage circuitry 160 and executing it. That is, the first receiving function 171 is a function implemented by the processing circuitry 170, where the processing circuitry 170 reads the program corresponding to the first receiving function 171 from the internal storage circuitry 160 and executes it. The second receiving function 172 is a function implemented by the processing circuitry 170, where the processing circuitry 170 reads the program corresponding to the second receiving function 172 from the internal storage circuitry 160 and executes it. The adjusting function 173 is a function implemented by the processing circuitry 170, where the processing circuitry 170 reads the program corresponding to the adjusting function 173 from the internal storage circuitry 160 and executes it. In other words, after reading each program, the processing circuitry 170 has the corresponding function illustrated in the processing circuitry 170 in FIG. 1. The processing functions performed by the first receiving function 171, the second receiving function 172, and the adjusting function 173 will be discussed below.

In the above embodiment, it has been described that the processing functions described above are implemented in the single processing circuitry 170, whereas such functions may be implemented by a configuration in which several independent processors are combined into processing circuitry and each processor executes the corresponding program.

The term "processor" used in the above description means, for example, a central processing unit (CPU), a graphics processing unit (GPU), or a circuit such as an application specific integrated circuit (ASIC) and a programmable logic device (for example, a simple programmable logic device (SPLD), a complex programmable logic device (CPLD), and a field programmable gate array (FPGA). The processor implements its functions by reading and executing the programs stored in the storage circuit. Note that, a computer program may be directly incorporated in a circuit of the processor instead of storing a computer program in the internal storage circuitry 160. In this case, the processor implements its functions by reading and executing the programs incorporated in the circuit. Note that, each processor in the present embodiment is not limited to the case where each processor is configured as a single circuit, and a plurality of independent circuits may be combined to configure a single processor so as to implement their functions. In addition, the components in each of the drawings may be integrated into a single processor so as to implement their functions.

The ultrasound diagnosis apparatus 1 according to the first embodiment performs ultrasound scanning for the Doppler mode, where the ultrasound diagnosis apparatus 1 images blood flow at high speed, high resolution, and high frame rate, to obtain blood flow information in which clutter components are significantly reduced compared with the ordinary Doppler method. Specifically, the first ultrasound scan implemented in the first embodiment is performed by repeating a scanning mode that is capable of collecting the reflected-wave data at the same positions across a plurality of frames, through the ultrasound transmission and reception in a scanning range of a plurality of scanning lines. More specifically, the first ultrasound scan implemented in the first embodiment is performed by repeating a scanning mode that performs one ultrasound transmission and reception for each scanning line in the scanning range of the scanning lines. Such a scanning mode is the same scanning mode as the second ultrasound scan implemented in the ordinary B-mode, and is the same scanning mode as a scanning mode that is implemented in the CFM method to increase the frame rate.

Figure 2:
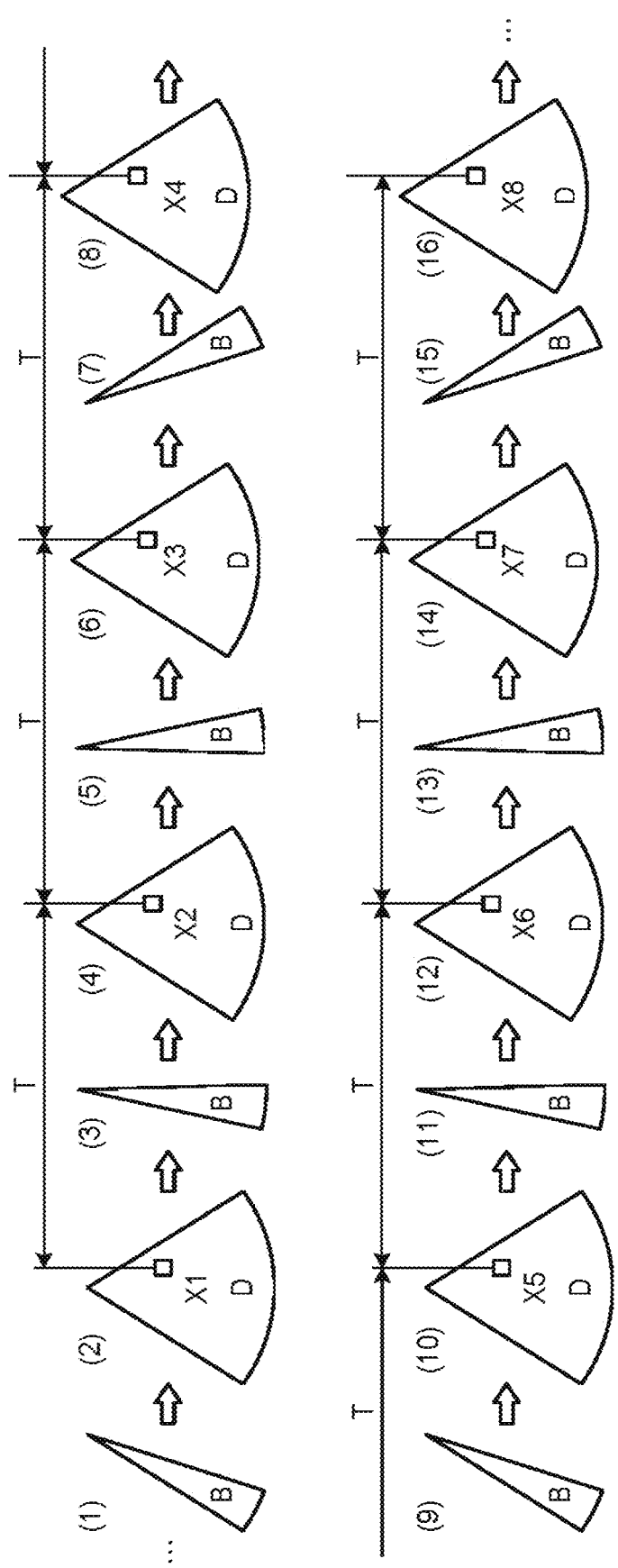
FIG. 2 is a view illustrating an example of ultrasound scanning for a Doppler mode according to the first embodiment.

FIG. 2 is a view illustrating an example of the ultrasound scanning for the Doppler mode according to the first embodiment. In the example illustrated in FIG. 2, as the second ultrasound scan, the processing circuitry 170 of the ultrasound diagnosis apparatus 1 causes the ultrasound probe 101 to perform ultrasound scans in the division ranges obtained by dividing the second scanning range, where each ultrasound scan is performed in a time-division manner during the first ultrasound scan. In other words, the processing circuitry 170 performs part of the second ultrasound scan during the first ultrasound scan, and completes one frame of the second ultrasound scan in a period for several frames of the first ultrasound scans. With this scanning mode, the ultrasound diagnosis apparatus 1 according to the first embodiment allows ultrasound transmission and reception conditions between the first ultrasound scan and the second ultrasound scan to be set independently. For instance, the ultrasound diagnosis apparatus 1 according to the first embodiment allows the second ultrasound scan to be performed under conditions based on the THI method. That is, the second ultrasound scan is performed under ultrasound transmission and reception conditions for performing the THI through the filtering described above. Furthermore, the second ultrasound scan is performed under ultrasound transmission and reception conditions for performing the THI based on an imaging method that transmits ultrasound at multiple rates for one scanning line. Examples of such an imaging method include the AM method, the PM method, and the AM/PM method described above, as well as a method using differential sound components.

An example of the above processing will be described with reference to FIG. 2. For instance, the processing circuitry 170 divides the second scanning range into four division ranges (i.e., a first division range to a fourth division range), based on, for example, instructions from the operator and initially set information. "B" illustrated in FIG. 2 indicates the range of an ultrasound scan (the second ultrasound scan) using transmission and reception conditions for the B-mode. "D" illustrated in FIG. 2 indicates the range of an ultrasound scan (the first ultrasound scan) using transmission and reception conditions for the color Doppler mode. For instance, "D" illustrated in FIG. 2 is the range of an ultrasound scan performed by the high-frame-rate method described above. That is, the first ultrasound scan illustrated in FIG. 2 performs one ultrasound transmission and reception for each scanning line, rather than transmitting ultrasound multiple times in the same direction and receiving reflected waves multiple times as the usual color Doppler method. As the first ultrasound scan, the processing circuitry 170 performs one ultrasound transmission and reception for each of the scanning lines of the first scanning range to perform the ultrasound scanning based on a method that obtains blood flow information using a plurality of frames of reflected waves (high-frame-rate method).

First, the processing circuitry 170 performs, as the second ultrasound scan, the ultrasound scan in the first division range (see (1) in FIG. 2), and performs the first ultrasound scan in the first scanning range (corresponding to one frame) (see (2) in FIG. 2). Next, the processing circuitry 170 performs, as the second ultrasound scan, the ultrasound scan in the second division range (see (3) in FIG. 2), and performs the first ultrasound scan in the first scanning range (corresponding to one frame) (see (4) in FIG. 2). Then, the processing circuitry 170 performs, as the second ultrasound scan, the ultrasound scan in the third division range (see (5) in FIG. 2), and performs the first ultrasound scan in the first scanning range (corresponding to one frame) (see (6) in FIG. 2). After that, the processing circuitry 170 performs, as the second ultrasound scan the ultrasound scan in the fourth division range (see (7) in FIG. 2), and performs the first ultrasound scan in the first scanning range (corresponding to one frame) (see (8) in FIG. 2). In this way, the processing circuitry 170 performs the second ultrasound scan for each of the division ranges during the first ultrasound scan in a time-division manner. Ultrasound scans from (9) to (16) in FIG. 2 correspond to a repetition of the ultrasound scans from (1) to (8), and thus the description will be omitted.

The processing circuitry 170 performs the first ultrasound scan at regular intervals. That is, "point X" on "a certain scanning line" of the first scanning range is scanned one time for each of the first ultrasound scans, i.e., (2), (4), (6), (8), (10), (12), (14), and (16) in FIG. 2, where the scan interval is controlled so as to be a fixed time "T". Specifically, the processing circuitry 170 equalizes the time involved in each divided scan performed in the second ultrasound scan so that the interval at which the first ultrasound scan is performed is equal. For instance, the processing circuitry 170 performs the control so that the time involved in each divided scan of the second ultrasound scan performed in (1), (3), (5), (7), (9), (11), (13), and (15) in FIG. 2 is equal. For each division range of the second scanning range, the processing circuitry 170 equalizes, for example, its size, the number of scanning lines, the scanning-line density, and its depth.

In the example illustrated in FIG. 2, tissue image data is generated every time the second ultrasound scan from the first division range "B" to the fourth division range "B" corresponding to the whole second scanning range is performed. For instance, when the second ultrasound scan is performed up to (7) in FIG. 2, the tissue image data of the whole second scanning range is generated based on information on the first division range "B" of (1), the second division range "B" of (3), the third division range "B" of (5), and the fourth division range "B" of (7). Furthermore, when the second ultrasound scan is performed up to (9) in FIG. 2, the tissue image data of the whole second scanning range is generated based on information on the first division range "B" of (9), the second division range "B" of (3), the third division range "B" of (5), and the fourth division range "B" of (7). Furthermore, when the second ultrasound scan is performed up to (11) in FIG. 2, the tissue image data of the whole second scanning range is generated based on information on the first division range "B" of (9), the second division range "B" of (11), the third division range "B" of (5), and the fourth division range "B" of (7). In this way, the processing circuitry 170 updates the tissue image data of each division range "B" every time the second ultrasound scan in each division range "B" is performed. If the THI is performed based on an imaging method that performs ultrasound transmission with multiple rates for one scanning line, the number of ultrasound transmissions for one frame of received signals increases. Thus, there is the need for increasing the divided number of the second scanning range, compared with the THI using the ordinary B-mode imaging and filtering. For instance, for the PM method, the second scanning range is changed from four divisions to eight divisions.

Furthermore, an image of moving-objects information (e.g., a blood flow image) is generated by filtering a data sequence of reflected-wave data at the same positions across a plurality of frames (e.g., the filtering using the eigenvector MTI filter). The data length of the data sequence used for outputting a piece of moving-object information can be optionally set (modified). Furthermore, the data sequence used for outputting the previous temporal moving-object information and the data sequence used for outputting the next temporal moving-object information can be overlapped, and the overlapped number can be optionally set (modified).

For instance, FIG. 2 illustrates that the data length of the data sequence is set to "4" and the overlapped number of the data sequence between displayed frames is set to "2". In this case, for instance, when the first ultrasound scans are performed up to (8) in FIG. 2, the moving-object information on position X in a first frame is generated by filtering the data sequence of position X1 in (2), position X2 in (4), position X3 in (6), and position X4 in (8). Subsequently, the moving-object information on the first frame is generated by generating the moving-object information for each position in the scanning range. Furthermore, when the first ultrasound scans are performed up to (12) in FIG. 2, the moving-object information on position X in a second frame is generated by filtering the data sequence of position X3 in (6), position X4 in (8), position X5 in (10), and position X6 in (12). Subsequently the moving-object information on the second frame is generated by generating the moving-object information for each position in the scanning range. Furthermore, when the first ultrasound scans are performed up to (16) in FIG. 2, the moving-object information on position X in a third frame is generated by filtering the data sequence of position X5 in (10), position X6 in (12), position X7 in (14), and position X8 in (16). Subsequently, the moving-object information on the third frame is generated by generating the moving-object information for each position in the scanning range. In this way, the processing circuitry 170 filters the data sequence having a data length of "4" to generate the moving-object information for each frame, every time the first ultrasound scans are performed by the number of times corresponding to the overlapped number "2".

In this way, the ultrasound diagnosis apparatus 1 according to the first embodiment images blood flow at high resolution and high frame rate, to perform the ultrasound scanning based on the high-frame-rate method for obtaining blood flow information in which clutter components are significantly reduced as compared with the ordinary Doppler method. That is, the ultrasound diagnosis apparatus 1 performs the second ultrasound scan in each division range in a time-division manner between the first ultrasound scans, each of which involves one ultrasound transmission and reception for each scanning line the scanning range, to generate blood flow images and tissue images at high resolution and high frame rate. Furthermore, the ultrasound diagnosis apparatus 1 filters the data sequence at the same positions across a plurality of frames using the eigenvector MTI filter, to generate blood flow images having significantly reduced clutter components.

However, for instance, the above-described ultrasound scanning for the Doppler mode can fail to display the blood flow information in a desired range of flow rate values (hereinafter, also referred to as a "flow rate range"). Specifically, in the ultrasound scanning for the Doppler mode, even if a blood flow image in a desired range of flow rate values is obtained, the range of flow rate values may be changed by adjusting other parameters, such as the size of a region of interest (ROI) and the position in the depth direction of the ROI. This can result in losing the blood flow information in the desired range of flow rate values.

For instance, when observing a blood flow image having a low flow rate, a medical doctor (operator) may want to observe a certain portion of the blood flow in greater detail. In this case, narrowing the ROI, which is the display range of the blood flow image, should further reduce clutter components and enable more detailed observation. This is because the eigenvector MTI filter described above determines the correlation matrix used to remove the clutter for each scanning range. That is, narrowing the ROI calculates the correlation matrix for the narrowed ROI, and thus should remove the clutter with enhanced accuracy. For this reason, if the doctor wants to observe the state of the blood flow in greater detail, the doctor attempts to observe it in greater detail by narrowing (tightening) the range of the ROI. However, parameters including the range of the ROI relate to the range of flow rate values, and thus changes in these parameters cause the range of flow rate values to be changed. This can result in losing the blood flow information in the desired range of flow rate values.

Figure 3:
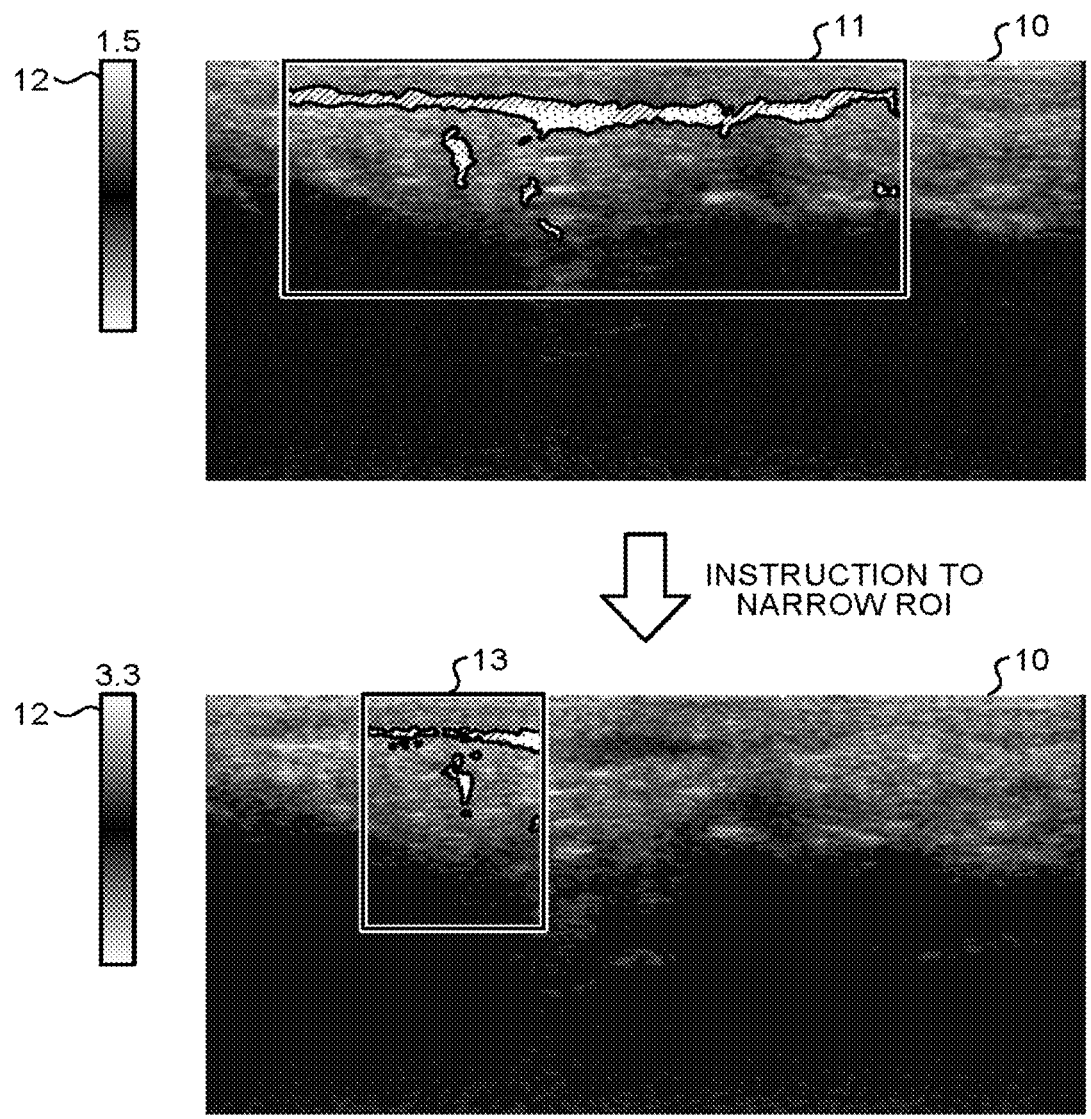
FIG. 3 is a view illustrating a conventional technique.

FIG. 3 is a view illustrating a conventional technique. FIG. 3 illustrates that the size of the ROI 11, in which a blood flow image is displayed on a tissue image 10, is changed by an instruction of the operator. That is, the upper stage in FIG. 3 illustrates the blood flow image in the ROI 11 before a change in its size, and the lower stage illustrates the blood flow image in the ROI 13 after the change in its size. In the ROI 11, the pixel value corresponding to the flow rate value of blood flow is assigned to the position at which the blood flow is detected. The range of flow rate values detected in the ROI 11 is indicated by a scale 12. That is, the scale 12 of the upper stage in FIG. 3 indicates that the blood flow in the range of up to 1.5 cm/s is displayed on the ROI 11, and the scale 12 of the lower stage in FIG. 3 indicates that the blood flow in the range up to 3.3 cm/s is displayed on the ROI 13.

In the example illustrated in the upper stage in FIG. 3, the state of the blood flow having a low flow rate up to 1.5 cm/s is accurately captured and displayed along the azimuthal direction of the ROI 11. When receiving an instruction to narrow the ROI from the operator, as illustrated in the lower stage in FIG. 3, the ROI 11 is narrowed into the ROI 13, and the blood flow in the ROI 13 is displayed.

When the length of the azimuthal direction is narrowed from the ROI 11 to the ROI 13, a scan period for one frame becomes shorter, and accordingly, the time "T", which is the scan interval between each frame, becomes shorter (see FIG. 2). This increases the pulse repetition frequency (PRF) of the first ultrasound scan, and accordingly, the upper limit of the flow rate range, which is a maximum detected flow rate, increases to 33 cm/s. In this way, in the ROI 13, the increase in the upper limit of the flow rate range results in losing the blood flow image having a low flow rate, which has been detected in the ROI 11. The reason why the increase in the flow rate range loses the blood flow image is that the range of pixel values allocated to the blood flow having a low flow rate has become narrower. Specifically, this is because pixel values allocated to the blood flow image in the flow rate range of up to 1.5 cm/s are shifted to pixel values having low luminance in the flow rate range of up to 3.3 cm/s.

In this way, if the blood flow image in the desired range of flow rate values is obtained, changes in various types of parameters can result in losing the blood flow information in the desired range of flow rate values.

To display the blood flow information in the desired range of flow rate values, the ultrasound diagnosis apparatus 1 according to the first embodiment implements the following processing functions. That is, the ultrasound diagnosis apparatus 1 receives an instruction to change the range of flow rate values, and performs an adjustment for maintaining the received range of flow rate values to be constant regardless of changes in any other parameter.

Referring back to the description of FIG. 1, the processing circuitry 170 according to the first embodiment performs the first receiving function 171, the second receiving function 172, and the adjusting function 173.

The first receiving function 171 receives a first instruction to change the range of flow rate values to be displayed, in display of blood flow information. For instance, the first receiving function 171 provides a user interface (UI) that is capable of changing the upper limit value of the range of flow rate values (the flow rate range) in response to an operation on the input device 102. The first receiving function 171 is an example of a first receiving unit.

As an example, the input device 102 will be described in a case that a knob on an operating panel of the ultrasound diagnosis apparatus 1 is used. In this case, the first receiving function 171 is associated with a rotation direction of the knob and variations of the upper limit value, and the rotation amount of the knob is associated with the variation amount of the upper limit value. When the operator rotates the knob in the direction toward which the upper limit value increases, the first receiving function 171 increases the upper limit value as a function of the rotation amount of the knob. When the operator rotates the knob in the direction toward which the upper limit value decreases, the first receiving function 171 lowers the upper limit value as a function of the rotation amount of the knob. The UI provided by the first receiving function 171 is not limited to the above example, and any technique for changing parameters through instructions from the operator may be applied. For instance, the first receiving function 171 may change the range of flow rate values upon an operation on a button, without limiting to the knob.

The second receiving function 172 receives a second instruction to change a parameter included in conditions for collecting blood flow information (scan conditions). For instance, the second receiving function 172 provides a UI that is capable of changing any parameters, such as the size of the ROI, the position of the ROI, the number of scanning lines (raster scanning lines) in the ROI (density), and the transmission frequency of ultrasound, in response to an operation cm the input device 102. The second receiving function 172 is an example of a second receiving unit. In other words, the second receiving function 172 receives the second instruction to change settings related to a region of interest. Furthermore, the functions of the second receiving function 172 is similar to those of the first receiving function 171 except for receiving an instruction to change the upper limit value of the range of flow rate values, and the description will be omitted.

The adjusting function 173 changes the range of flow rate values in response to the first instruction when the first receiving function 171 receives the first instruction, and performs the adjustment for maintaining the changed range of flow rate values also when the second receiving function 172 receives the second instruction to change any parameter related to the range of flow rate values. In other words, the adjusting function 173 changes the range of flow rate values in response to the first instruction when the first receiving function 171 receives the first instruction, and performs the adjustment for maintaining the range of flow rate values when the second receiving function 172 receives the second instruction. For instance, when receiving, as the second instruction, a change instruction to increase the range of flow rate values, the adjusting function 173 performs the adjustment for maintaining the range of flow rate values, which has been changed by the first instruction. The adjusting function 173 is an example of an adjusting unit.

For instance, the adjusting function 173 performs a comparison of a first transmission and reception time for each scanning line (hereinafter, also referred to as "T1" as necessary) with a second transmission and reception time for each scanning line (hereinafter, also referred to as "T2" as necessary), and performs the adjustment depending on the result of the comparison. The first transmission and reception time is based on the scan conditions other than the range of flow rate values changed by the first instruction, and the second transmission and reception time is based on the range of flow rate values changed by the first instruction. For instance, the first transmission and reception time (T1) and the second transmission and reception time (T2) are calculated by the processing circuitry 170, and individually stored in the internal memory of the processing circuitry 170.

The first transmission and reception time (T1) is the transmission and reception time required to transmit and receive ultrasound for each scanning line in the ROI, and depends on the scan conditions other than the flow rate range changed by the first instruction. For instance, in performing the first ultrasound scan described above, the processing circuitry 170 calculates various types of parameters related to the ultrasound scan. Furthermore, the processing circuitry 170 changes parameters in response to the second instruction to change various types of parameters, and changes other parameters related to the changed parameter. For instance, at the start of the first ultrasound scan, the processing circuitry 170 calculates various types of parameters related to the ultrasound scan, based on predetermined conditions in the apparatus and conditions including the size of the ROI received from the operator. Furthermore, for example, when receiving the second instruction from the operator to narrow the ROI in the azimuthal direction, the processing circuitry 170 narrows the ROI in the azimuthal direction in response to the received second instruction, and reduces the number of scanning lines in the ROI to maintain the scanning-line density in the ROI. In this way, the processing circuitry 170 determines various types of parameters, such as the depth of a tissue image (B-mode image), the size of the ROI for the Doppler mode, the position of the ROI, the number of scanning lines (raster scanning lines) in the ROI, and the transmission frequency of ultrasound. The first transmission and reception time (T1) is determined by the processing circuitry 170 along with these parameters, and stored and updated in the internal memory.

The second transmission and reception time (T2) is the transmission and reception time depending on the flow rate range changed by the first instruction. For instance, when the upper limit of the flow rate range is increased by the first instruction, because of increased PRF, the processing circuitry 170 shortens the second transmission and reception time (T2) (calculates shorter T2). In contrast, when the upper limit of the flow rate range is lowered by the first instruction, because of reduced PRF, the processing circuitry 170 lengthens the second transmission and reception time (T2) (calculates longer T2). In this way, the second transmission and reception time (T2) is determined by the processing circuitry 170, and stored and updated in the internal memory, independently from the first transmission and reception time (T1).

The adjusting function 173 individually acquires the first transmission and reception time (T1) and the second transmission and reception time (T2) from the internal memory. The adjusting function 173 then performs a comparison of the first transmission and reception time (T1) with the second transmission and reception time (T2). The adjusting function 173 maintains the other parameters (other than transmission and reception time) included in the scan conditions when the second transmission and reception time (T2) is larger than the first transmission and reception time (T1), and reduces the number of scanning lines, which is a parameter included in the scan conditions, when the second transmission and reception time (T2) is smaller than the first transmission and reception time (T1). The processing performed by the adjusting function 173 will now be described with reference to FIG. 4 to FIG. 8.

Figure 4:
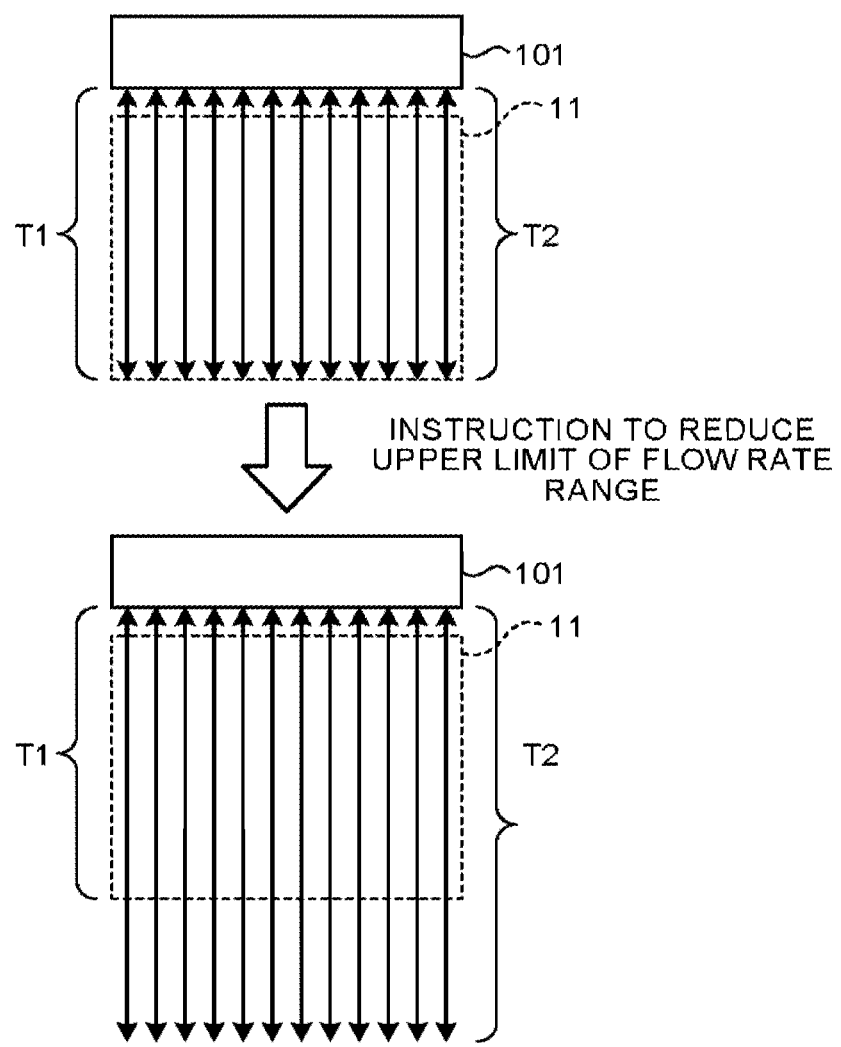
FIG. 4 is a view illustrating a process of an adjusting function according to the first embodiment.
Figure 6:
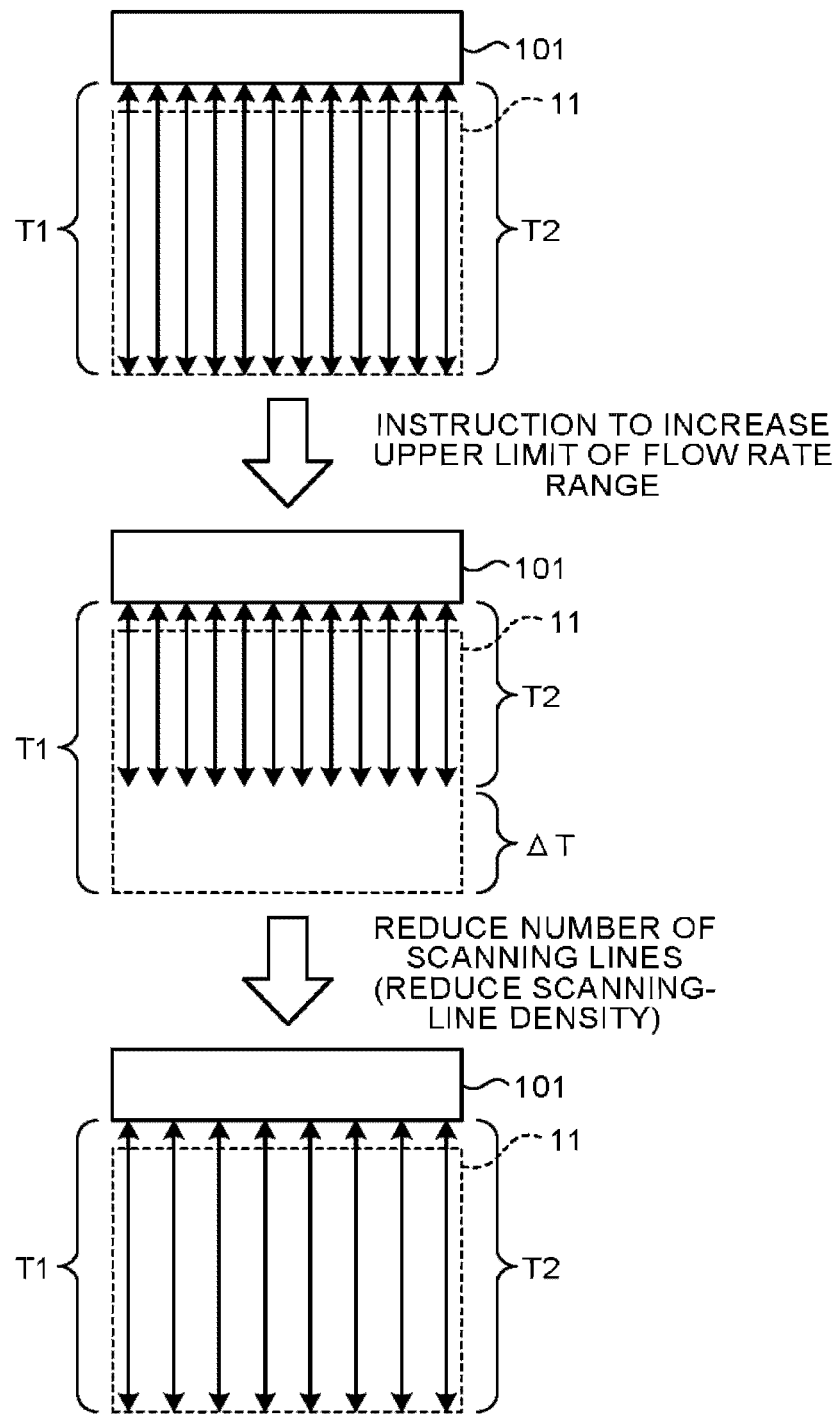
FIG. 6 is a view illustrating the process of the adjusting function according to the first embodiment.
Figure 7:
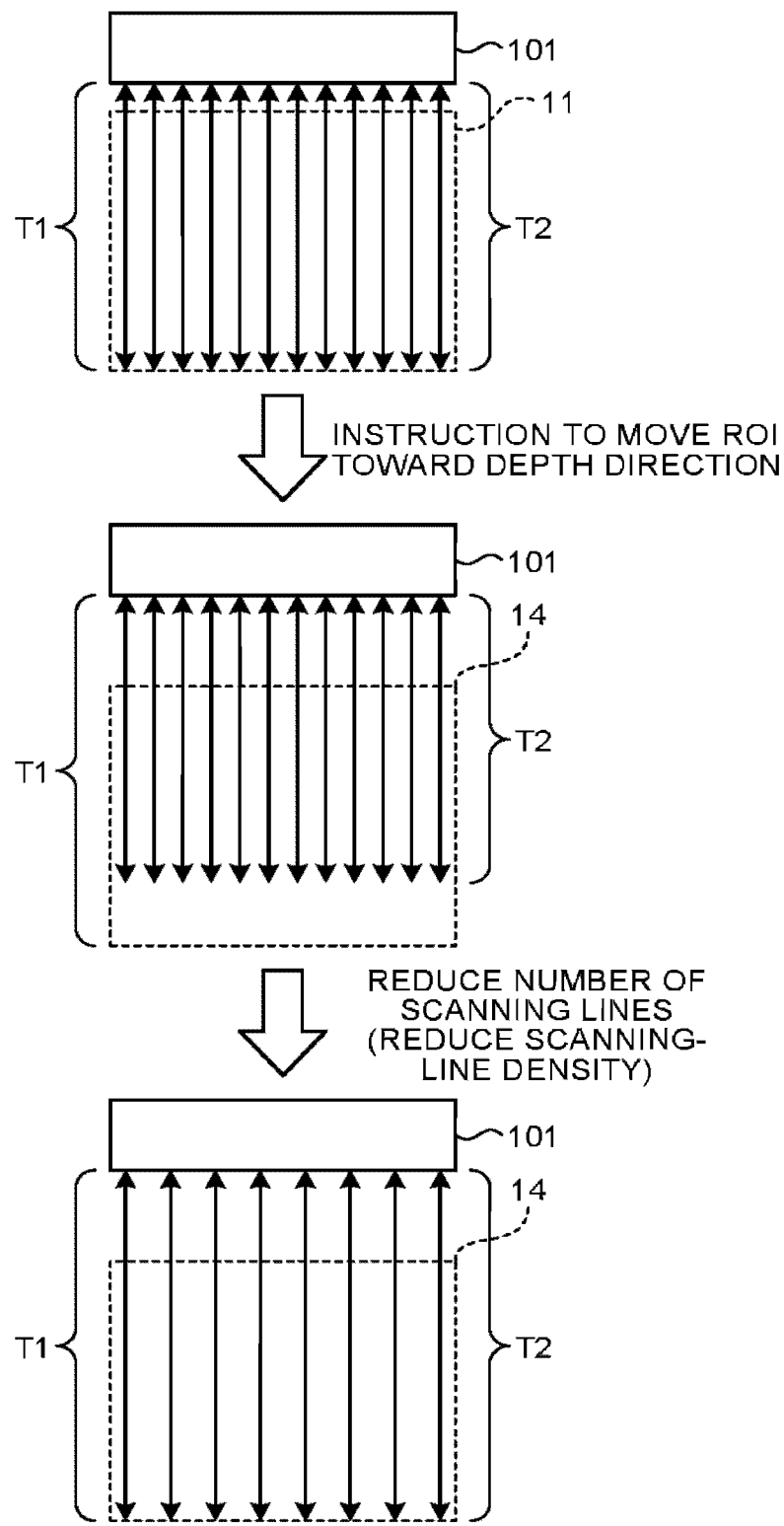
FIG. 7 is a view illustrating the process of the adjusting function according to the first embodiment.
Figure 8:
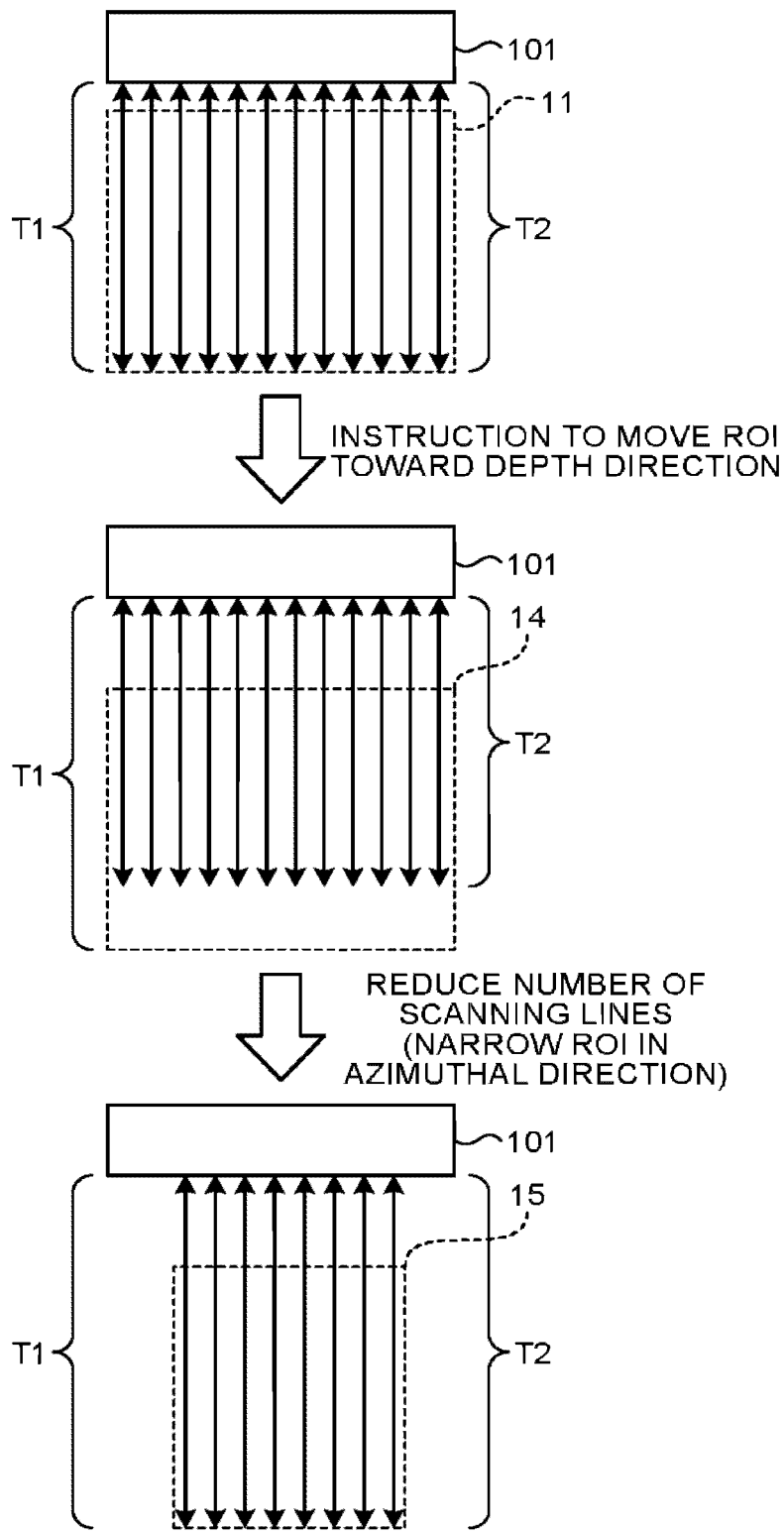
FIG. 8 is a view illustrating the process of the adjusting function according to the first embodiment.

FIG. 4 to FIG. 8 are views illustrating the processing performed by the adjusting function 173 according to the first embodiment. FIG. 4 to FIG. 8 illustrates various types of parameters related to the ultrasound scan in the ROI 11. FIG. 4 and FIG. 5 illustrate the process in a case where the second transmission and reception time (T2) is larger than the first transmission and reception time (T1), and FIG. 6 to FIG. 8 illustrate the process in a case where the second transmission and reception time (T2) is smaller than the first transmission and reception time (T1).

FIG. 4 illustrates that an instruction to lower the upper limit of the flow rate range is issued. As illustrated in the upper stage in FIG. 4, before the instruction to lower the upper limit of the flow rate range is issued, the ultrasound probe 101 performs the ultrasound transmission and reception for each scanning line in the ROI 11 in the first transmission and reception time (T1). When the first receiving function 171 receives the instruction to lower the upper limit of the flow rate range, as illustrated in the lower stage in FIG. 4, the processing circuitry 170 calculates the second transmission and reception time (T2) longer than the first transmission and reception time (T1) because of reduced PRF. In this case, the adjusting function 173 sets the transmission and reception time of the parameters included in the scan conditions to the second transmission and reception time (T2), and maintains (does not change) the other parameters. Subsequently, the adjusting function 173 sends the set scan conditions having the second transmission and reception time (T2) to the transmitting and receiving circuitry 110, the B-mode processing circuitry 120, and the Doppler processing circuitry 130, to cause the ultrasound scanning to be performed under such scan conditions. That is, the adjusting function 173 causes the ultrasound transmission and reception for each scanning line to be performed in the second transmission and reception time (T2).

In this way, when the second transmission and reception time (T2) is larger than the first transmission and reception time (T1), the adjusting function 173 maintains the other parameters, and causes the ultrasound transmission and reception to be performed in the second transmission and reception time (T2). In this case, when the first transmission and reception time (T1) is lengthened by an instruction to change any other parameter, any value that is not larger than the second transmission and reception time (T2) enables the adjusting function 173 maintain the changed flow rate range.

FIG. 5 illustrates that an instruction to narrow the ROI is issued. In this case, it will be described that the flow rate range has been changed by the operator prior to such an instruction and the ultrasound transmission and reception is performed in the second transmission and reception time (T2).

As illustrated in the upper stage in FIG. 5, before the instruction to narrow the ROI, the ultrasound probe 101 performs the ultrasound transmission and reception for each scanning line in the ROI 11 in the second transmission and reception time (T2). When the second receiving function 172 receives the instruction to narrow the ROI, as illustrated in the lower stage in FIG. 5, the reduced number of scan lines results in reduced PRF, and accordingly, the processing circuitry 170 calculates the second transmission and reception time (T2) longer than the first transmission and reception time (T1). In this case, the adjusting function 173 sets the transmission and reception time of the parameters included in the scan conditions to the second transmission and reception time (T2), and maintains (does not change) the other parameters. Subsequently, the adjusting function 173 sends the set scan conditions having the second transmission and reception time (T2) to the transmitting and receiving circuitry 110, the B-mode processing circuitry 120, and the Doppler processing circuitry 130, to cause the ultrasound scanning to be performed under such scan conditions. That is, the adjusting function 173 causes the ultrasound transmission and reception for each scanning line to be performed in the second transmission and reception time (T2).

In this way, the adjusting function 173 calculates the longer second transmission and reception time (T2) when the number of scanning lines decreases. This enables the adjusting function 173 to prevent the scan interval between each frame from becoming shorter and maintain the changed flow rate range.

FIG. 6 illustrates that an instruction to increase the upper limit of the flow rate range is issued. As illustrated in the upper stage in FIG. 6, before the instruction to increase the upper limit of the flow rate range, the ultrasound probe 101 performs the ultrasound transmission and reception for each scanning line in the ROI 11 in the first transmission and reception time (T1). When the first receiving function 171 receives the instruction to increase the upper limit of the flow rate range, the PRF increases. If the number of scanning lines is maintained, the ultrasound transmission and reception time cannot be maintained, and thus the processing circuitry 170 calculates the second transmission and reception time (T2) shorter than the first transmission and reception time (T1) (the middle stage in FIG. 6). In this case, as illustrated in the lower stage in FIG. 6, the adjusting function 173 maintains the second transmission and reception time (T2) (maintains it to the same extent as the first transmission and reception time (T1)) by reducing the scanning-line density included in the scan conditions. In the illustrated example, the adjusting function 173 reduces the number of scanning lines from 12 to 8. Subsequently, the adjusting function 173 sends the scan conditions having the reduced scanning-line density to the transmitting and receiving circuitry 110, the B-mode processing circuitry 120, and the Doppler processing circuitry 130, to cause the ultrasound scanning to be performed under such scan conditions.

The process of calculating the changed number of scanning lines will be specifically described. First, assuming that the number of scanning lines is maintained, the adjusting function 173 calculates a shortage of transmission and reception time using equation (1) as follows. In equation (1), ΔT, T1, and T2 respectively represent the shortage of transmission and reception time, the first transmission and reception time, and the second transmission and reception time. Rnum1 represents the number of scanning lines before the reception of the instruction to increase the upper limit of the flow rate range.

$$\Delta T = T1 \times Rnum1 - T2 \times Rnum1 \quad (1)$$

Subsequently, the adjusting function 173 calculates how many scanning lines correspond to the shortage of transmission and reception time (ΔT) using equation (2) as follows. In equation (2), Rnum2 represents the number of scanning lines for which the transmission and reception can be performed in the shortage of transmission and reception time (ΔT).

$$Rnum2 = \Delta T / T1 \quad (2)$$

The adjusting function 173 then calculates the number of scanning lines after the change in the flow rate range using equation (3) as follows. In equation (3), Rnum3 represents the number of scanning lines after the change in the flow rate range.

$$Rnum3 = Rnum1 - Rnum2 \quad (3)$$

In this way, when the second transmission and reception time (T2) is smaller than the first transmission and reception time (T1), the adjusting function 173 maintains the second transmission and reception time (T2) by reducing the number of scanning lines (density). Specifically, the adjusting function 173 reduces the number of scanning lines, while maintaining the length of the ROI in the azimuthal direction.

As described above, in reducing the number of scanning lines, the adjusting function 173 may give a warning. For instance, when the number of scanning lines included in the scan conditions is reduced, the adjusting function 173 displays messages, such as "image quality can be deteriorated", on the display 103. When the number of scanning lines is reduced, the adjusting function 173 does not always give a warning, but may give a warning, for example, after allowing a certain extent of reduction. That is, the adjusting function 173 may store a threshold of the number of scanning lines (or the density), and may give a warning when the number of scanning lines included in the scan conditions has become equal to or less than the threshold.

FIG. 7 illustrates that an instruction to move the ROI toward the depth direction is issued. In this case, it will be described that the flow rate range has been changed by the operator prior to such an instruction and the ultrasound transmission and reception are performed in the second transmission and reception time (T2).

As illustrated in the upper stage in FIG. 7, before the instruction to move the ROI toward the depth direction is issued, the ultrasound probe 101 transmits and receives ultrasound for each scanning line in the ROI 11 in the second transmission and reception time (T2). When the second receiving function 172 receives the instruction to move the ROI toward the depth direction, as illustrated in the middle stage in FIG. 7, the processing circuitry 170 calculates the first transmission and reception time (T1) longer than the second transmission and reception time (T2), with the move of the ROI 14 toward the depth direction. In this case, as illustrated in the lower stage in FIG. 7, the adjusting function 173 lengthens the second transmission and reception time (T2) to the same extent as the first transmission and reception time (T1), by reducing the number of scanning lines (density) included in the scan conditions. In the illustrated example, the adjusting function 173 reduces the number of scanning lines from 12 to 8. Subsequently, the adjusting function 173 sends the scan conditions having the reduced scanning-line density to the transmitting and receiving circuitry 110, the B-mode processing circuitry 120, and the Doppler processing circuitry 130, to cause the ultrasound scanning to be performed under such scan conditions.

In this way, when the second transmission and reception time (T2) is smaller than the first transmission and reception time (T1), the adjusting function 173 maintains the second transmission and reception time (T2) to the same extent as the first transmission and reception time (T1) by reducing the number of scanning lines (density). Specifically, the adjusting function 173 reduces the number of scanning lines, while maintaining the length of the ROI in the azimuthal direction. With this configuration, the adjusting function 173 adjusts the flow rate range to be the desired range, while maintaining the size of the ROI and the frame rate, for example.

FIG. 8 illustrates that an instruction to move the ROI toward the depth direction is issued. FIG. 8 corresponds to a variation of FIG. 7.

As illustrated in the upper stage in FIG. 8, before the instruction to move the ROI toward the depth direction, the ultrasound probe 101 performs the ultrasound transmission and reception for each scanning line in the ROI 11 in the second transmission and reception time (T2). When the second receiving function 172 receives the instruction to move the ROI toward the depth direction, as illustrated in the middle stage in FIG. 8, the processing circuitry 170 calculates the first transmission and reception time (T1) longer than the second transmission and reception time (T2), with the move of the ROI 14 toward, the depth direction. In this case, as illustrated in the lower stage in FIG. 8, the adjusting function 173 reduces the number of scanning lines and lengthens the second transmission and reception time (T2) to the same extent as the first transmission and reception time (T1), by narrowing an ROI 15 included in the scan conditions in the azimuthal direction. In the illustrated example, the adjusting function 173 reduces the number of scanning lines from 12 to 8. Subsequently, the adjusting function 173 sends the scan conditions having the narrowed ROI to the transmitting and receiving circuitry 110, the B-mode processing circuitry 120, and the Doppler processing circuitry 130, to cause the ultrasound scanning to be performed under such scan conditions.

In this way, when the second transmission and reception time (T2) is smaller than the first transmission and reception time (T1), the adjusting function 173 maintains the second transmission and reception time (T2) to the same extent as the first transmission and reception time (T1) by narrowing the ROI in the azimuthal direction and reducing the number of scanning lines. With this configuration, the adjusting function 173 adjusts the flow rate range to be the desired range with maintained image quality (raster density) by narrowing the ROI in the azimuthal direction. That is, the instruction to move the ROI toward the depth direction is regarded as an action to bring the ROI close to a target. Thus, the somewhat narrowed ROI has its few drawbacks, and instead, yields an advantage of preventing the deterioration of the image quality.

Figure 9:
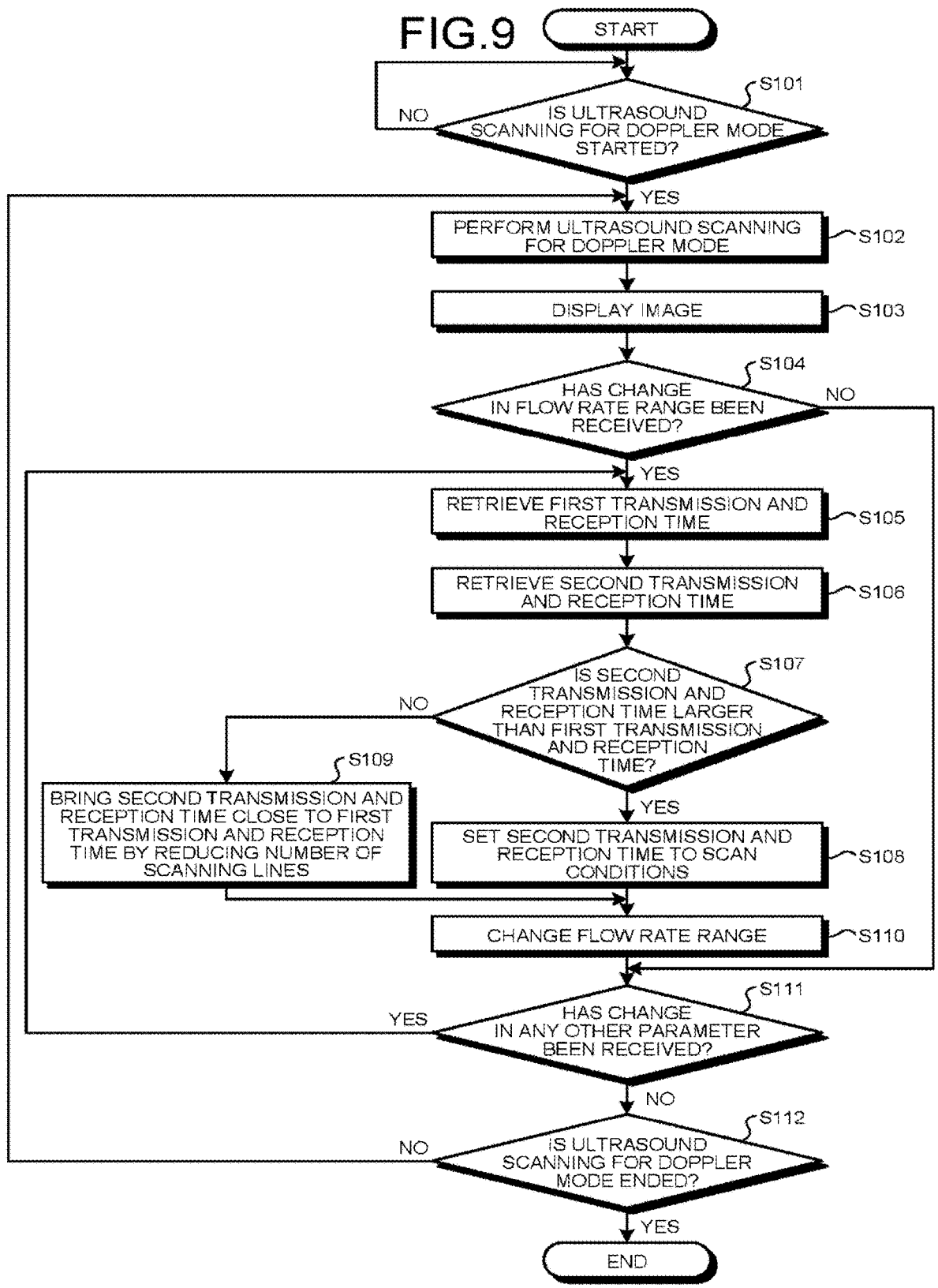
FIG. 9 is a flowchart illustrating a process of the ultrasound diagnosis apparatus according to the first embodiment.

FIG. 9 is a flowchart illustrating the process performed by the ultrasound diagnosis apparatus 1 according to the first embodiment. For instance, the process illustrated in FIG. 9 is started when a start instruction to start the ultrasound scanning for the Doppler mode is received from the operator.

In step S101, the processing circuitry 170 determines whether the start instruction to start the ultrasound scanning for the Doppler mode has been received. When the start instruction to start the ultrasound scan for the Doppler mode has been received, the processing circuitry 170 starts the processing from Step S102. If Step S101 is false, the process from Step S102 is not started, and the functions of the processing circuitry 170 are in wait state.

If step S101 is true, the processing circuitry 170 performs the ultrasound scanning for the Doppler mode in Step S102. For instance, the processing circuitry 170 controls the ultrasound scanning by controlling, for example, the transmitting and receiving circuitry 110, the B-mode processing circuitry 120, and the Doppler processing circuitry 130.

In Step S103, the processing circuitry 170 displays an image. For instance, the processing circuitry 170 displays the image generated by the image generating circuitry 140 on the display 103, based on the reflected-wave data collected through the ultrasound scanning for the Doppler mode. Specifically, the processing circuitry 170 displays a tissue image and displays a blood flow image on the indicated region (ROI) in the tissue image 10.

In Step S104, the first receiving function 171 determines whether the change in flow rate range has been received. When the change in flow rate range has been received, the first receiving function 171 performs the process from Step S105. If Step S104 is false, the process moves to the processing at Step S111.

If Step S104 is true, in Step S105, the adjusting function 173 retrieves the first transmission and reception time (T1) from the internal memory of the processing circuitry 170. The first transmission and reception time (T1) is the transmission and reception time required to transmit and receive ultrasound for each scanning line in the ROI, and depends on the scan conditions other than the flow rate range changed by the first instruction.

In Step S106, the adjusting function 173 retrieves the second transmission and reception time (T2) from the internal memory of the processing circuitry 170. For example, the second transmission and reception time (T2) is calculated with the flow rate range changed by the first instruction.

In Step S107, the adjusting function 173 performs a comparison of the first transmit and reception time (T1) with the second transmission and reception time (T2), and determines whether the second transmission and reception time (T2) is larger than the first transmission and reception time (T1). When the second transmission and reception time (T2) is larger than the first transmission and reception time (T1), the adjusting function 173 performs the processing at Step S108. In contrast, when the second transmission and reception time (T2) is smaller than the first transmission and reception time (T1), the adjusting function 173 performs the processing at S109.

If Step S107 is true, in Step S108, the adjusting function 173 sets the second transmission and reception time (T2) to the scan conditions. Specifically, the adjusting function 173 sets the transmission and reception time of the parameters included in the scan conditions to the second transmission and reception time (T2), and maintains the other parameters. With this configuration, the adjusting function 173 causes the transmitting and receiving circuitry 110, the B-mode processing circuitry 120, and the Doppler processing circuitry 130 to perform the ultrasound scanning under the set scan conditions having the second transmission and reception time (T2).

If Step S107 is false, in Step S109, the adjusting function 173 maintains the second transmission and reception time (T2) so as to be brought close to the first transmission and reception time (T1) by reducing the number of scanning lines. The adjusting function 173 then changes the number of scanning lines in the scan conditions. With this configuration, the adjusting function 173 causes the transmitting and receiving circuitry 110, the B-mode processing circuitry 120, and the Doppler processing circuitry 130 to perform the ultrasound scanning under the scan conditions having the changed number of scanning lines.

In Step S110, the adjusting function 173 changes the flow rate range. For instance, the adjusting function 173 changes the upper limit of the flow rate range in response to the first instruction received by the first receiving function 171.

In Step S111, the second receiving function 172 determines whether changes in any other parameter other than the flow rate range have been received. When changes in any other parameter have been received, the processing circuitry 170 performs the process from Step S105. If Step S111 is false, the process moves to the processing at S112.

If Step S111 is false, in step S112, the processing circuitry 170 determines whether an end instruction to end the ultrasound scanning for the Doppler mode has been received. When the end instruction to end the ultrasound scanning for the Doppler mode has been received, the processing circuitry 170 ends the process in FIG. 9. If Step S112 is false, the process moves to the processing at Step S102.

As described above, the ultrasound diagnosis apparatus 1 according to the first embodiment receives the instruction to change the range of flow rate values, and performs the adjustment for maintaining the received range of flow rate values to be constant regardless of changes in any other parameter. This enables the ultrasound diagnosis apparatus 1 according to the first embodiment to display the blood flow information in the desired range of flow rate values.

Furthermore, for example, the ultrasound diagnosis apparatus 1 performs a comparison of the first transmission and reception time with the second transmission and reception time to perform the adjustment depending on the result of the comparison. With this configuration, the ultrasound diagnosis apparatus 1 defects the shortage of transmission and reception time required to display the blood flow information in the desired range of flow rate values, and thus performs the adjustment depending on this shortage.

Figure 10:
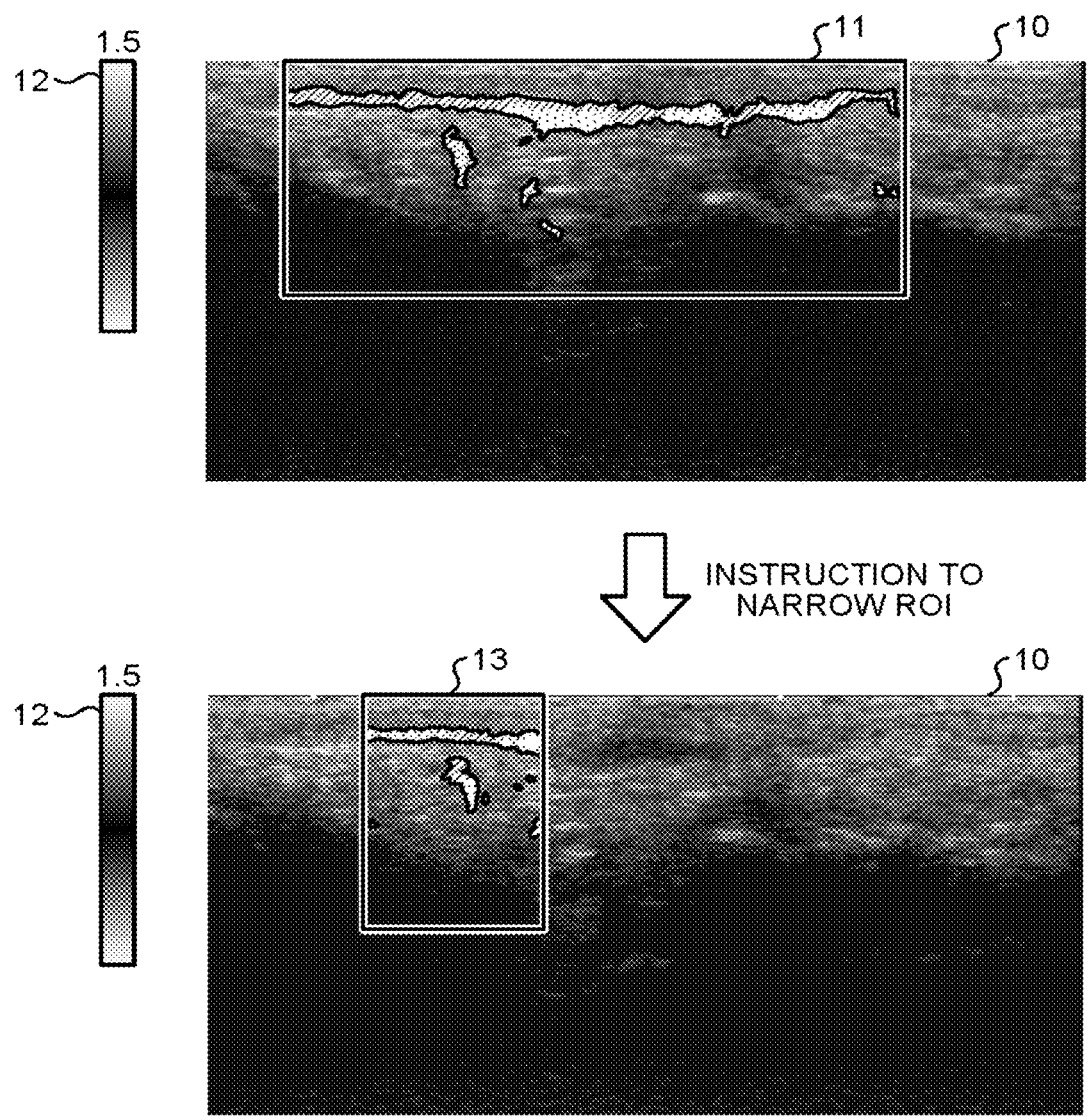
FIG. 10 is a view illustrating an example application of the ultrasound diagnosis apparatus according to the first embodiment.

FIG. 10 is a view illustrating an example application of the ultrasound diagnosis apparatus 1 according to the first embodiment. FIG. 10 illustrates that the size of the ROI 11, in which the blood flow image is displayed on the tissue image 10, is changed by an instruction of the operator. That is, the upper stage in FIG. 10 illustrates the blood flow image in the ROI 11 before the change in its size, and the lower stage illustrates the blood flow image in the ROI 13 after the change in its size. In the ROI 11 and the ROI 13, the pixel value corresponding to the flow rate value of the blood flow is assigned to the position at which the blood flow is detected. The range of flow rate values detected in the ROI 11 and the ROI 13 (hereinafter, also referred to as "the flow rate range") is indicated by the scale 12. In FIG. 10, the process after the change in the upper limit of the flow rate range will be described, where the upper limit of the flow rate range is changed to 1.5 cm/s by an instruction to change the flow rate range.

In the example of the upper stage in FIG. 10, the state of the blood flow with a low flow rate up to 1.5 cm/s is accurately captured and displayed along the azimuthal direction of the ROI 11. When receiving the instruction to narrow the ROI from the operator, as illustrated in the lower stage in FIG. 10, the ROI 11 is narrowed into the ROI 13, and the blood flow in the ROI 13 is detected and displayed.

When the length of the azimuthal direction is narrowed from the ROI 11 to the ROI 13, the adjusting function 173 of the ultrasound diagnosis apparatus 1 according to the first embodiment calculates the longer second transmission and reception time (T2) as a function of the reduced number of scanning lines. This enables the ultrasound diagnosis apparatus 1 to prevent the scan interval between each frame from becoming shorter, and eliminate an increase in the changed flow rate range to maintain the flow rate range. Thus, as illustrated in the lower stage in FIG. 10, the ultrasound diagnosis apparatus 1 according to the first embodiment provides the ROI 13 in which the blood flow having a low flow rate is displayed to the same extent as the blood flow in the ROI 11. For instance, this enables the ultrasound diagnosis apparatus 1 to provide blood flow images having the flow rate that a medical doctor desires when using the blood flow having a low flow rate for diagnosis.

Other Embodiments

Various different embodiments other than the above-described embodiment may be implemented.

A case where an instruction to increase the flow rate range is disabled (inhibition process).

For example, it has been described that the first embodiment described above is capable of supporting both instructions of increasing and reducing the flow rate range, but embodiments are not limited to this. For instance, the instruction to increase the flow rate range may be disabled.

In this case, the adjusting function 173 of the ultrasound diagnosis apparatus 1 performs the following process. For instance, the adjusting function 173 gives a warning when the first instruction received by the first receiving function 171 is the instruction to increase the upper limit of the range of flow rate values. When the first instruction received is the instruction to lower the upper limit of the range of flow rate values, the adjusting function 173 lowers the upper limit of the range of flow rate values, and performs the adjustment for maintaining the range of flow rate values having the lowered upper limit also when the second receiving function 172 receives the second instruction to change parameters related to the range of flow rate values.

That is, the adjusting function 173 lengthens the second transmission and reception time (T2) through the process described above when the first receiving function 171 receives the instruction to lower the upper limit of the flow rate range. Thereafter, any instruction other than the instructions to change the range of flow rate values will maintain the lengthened second transmission and reception time (T2). In contrast, when the first receiving function 171 receives the instruction to increase the upper limit of the flow rate range, the adjusting function 173 fails to increase the flow rate range, and gives a warning. Thus, the ultrasound diagnosis apparatus 1 can exclude the probable deterioration of the image quality, while allowing the flow rate values to be reduced to the desired values.

Furthermore, the ultrasound diagnosis apparatus 1 may have an operating mode that is capable of supporting both instructions to increase and reduce the flow rate range and an operating mode that disables only the instruction to increase the flow rate range, and enable these operating modes to be selected on UIs.

Furthermore, in a case (operating mode) that is capable of supporting both instructions to increase and reduce the flow rate range, if the ultrasound diagnosis apparatus 1 is forced to reduce the resolution by the instruction to increase the flow rate range, the ultrasound diagnosis apparatus 1 may disable the instruction (inhibition process). For instance, in a situation where "T1<T2" under predetermined conditions in the apparatus and various types of conditions received from the operator, even if the flow rate range is increased, there is no need for reducing the resolution (the number of scanning lines). That is, in a range that holds "T1<T2", when the first receiving function 171 receives the instruction to increase the flow rate range, the adjusting function 173 increases the flow rate range in response to the instruction. In contrast, in a situation where the increased flow rate range results in "T1>T2", reducing the resolution (the number of scanning lines) is necessary. That is, in a range that does not hold "T1>T2", when the first receiving function 171 receives the instructor to increase the flow rate range, the adjusting function 173 fails to increase the flow rate range (inhibition process). In this way, the ultrasound diagnosis apparatus 1 inhibits instructions that involve sacrificing the resolution, while supporting both instructions to increase and reduce the flow rate range in a range where the resolution is not sacrificed. This enables the ultrasound diagnosis apparatus 1 to support increasing and reducing the flow rate range as necessary, without sacrificing the resolution.

Furthermore, each component of each device is conceptually illustrated based on its function, and is not necessarily required to physically configured as illustrated. In other words, a specific mode for dispersion and integration of the devices is not limited to the illustrated one, and all or part of the devices can be functionally or physically dispersed and integrated in arbitrary units depending on various kinds of loads, usage conditions, and any other parameter. In addition, all or any part of each processing function executed by each device may be implemented by a CPU and a computer program analyzed and executed by the CPU, or implemented as hardware by wired logic.

Furthermore, among the processing contents described in the above-mentioned embodiments, all or part of the processing that is described as being automatically executed can also be manually executed, or all or part of the processing that is described as being manually executed can also be automatically executed by a known method. In addition, the processing procedures, the control procedures, the specific names, and the information including various kinds of data and parameters described herein and illustrated in the accompanying drawings can be arbitrarily changed unless otherwise specified.

Furthermore, the ultrasound imaging method described in the above-mentioned embodiment can be implemented by a personal computer or a workstation computer executing an ultrasound imaging method prepared in advance. The ultrasound imaging method can be distributed via a network such as the Internet. Furthermore, the ultrasound imaging method can be recorded in a computer-readable recording medium, such as a hard disk, a flexible disk (FD), a CD-ROM, an MO, and a DVD, and executed by a computer reading the program from the recording medium.

According to at least one of the embodiments described above, blood flow information can be displayed in a desired range of flow rate values.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnosis apparatus comprising:
   Doppler processing circuitry configured to filter a data sequence of reflected-wave data at same positions across a plurality of frames to collect blood flow information in a predetermined region of interest; and
   processing circuitry configured to
      determine a first transmission and reception time required to transmit and receive ultrasound for a scanning line in an ultrasound scan performed to acquire the reflected-wave data in the predetermined region of interest,
      receive a first instruction to change a range of flow rate values to be displayed, in display of the blood flow information,
      determine a second transmission and reception time for the scanning line based on the range of flow rate values changed by the first instruction,
      receive a second instruction to change a setting related to the predetermined region of interest,
      when receiving the first instruction, change the range of flow rate values in response to the first instruction,
      when receiving the second instruction, perform a comparison of the first transmission and reception time for the scanning line with the second transmission and reception time for the scanning line, the first transmission and reception time being based on scan conditions other than the range of flow rate values changed by the first instruction, and
      perform, based on a result of the comparison, an adjustment of at least one parameter included in the scan conditions for maintaining the range of flow rate values changed by the first instruction, even if the second instruction is an instruction to increase the range of flow rate values.

2. The ultrasound diagnosis apparatus according to claim 1, wherein
   the processing circuitry maintains parameters other than transmission and reception time included in the scan conditions when the second transmission and reception time is larger than the first transmission and reception time and reduces a number of scanning lines when the second transmission and reception time is smaller than the first transmission and reception time, and the number of scanning lines is a parameter included in the scan conditions, and
   the Doppler processing circuitry collects the blood flow information under the scan conditions adjusted by the processing circuitry.

3. The ultrasound diagnosis apparatus according to claim 2, wherein the processing circuitry maintains a length of the predetermined region of interest in an azimuthal direction for collecting the blood flow information and reduces the number of scanning lines when the second transmission and reception time is smaller than the first transmission and reception time.

4. The ultrasound diagnosis apparatus according to claim 2, wherein the processing circuitry shortens a length of the predetermined region of interest in an azimuthal direction for collecting the blood flow information and reduces the number of scanning lines when the second transmission and reception time is smaller than the first transmission and reception time.

5. The ultrasound diagnosis apparatus according to claim 2, wherein the processing circuitry reduces the number of scanning lines when the second transmission and reception time is smaller than the first transmission and reception time and gives a warning when the reduced number of scanning lines is equal to or less than a predetermined number.

6. An ultrasound diagnosis apparatus comprising:
   Doppler processing circuitry configured to filter a data sequence of reflected-wave data at same positions across a plurality of frames to collect blood flow information; and
   processing circuitry configured to
      determine a first transmission and reception time required to transmit and receive ultrasound for a scanning line in an ultrasound scan performed to acquire the reflected-wave data,
      receive a first instruction to change a range of flow rate values to be displayed, in display of the blood flow information,
      determine a second transmission and reception time for the scanning line based on the range of flow rate values changed by the first instruction,
      receive a second instruction to change a parameter included in conditions for collecting the blood flow information,
      give a warning when the first instruction is an instruction to increase an upper limit of the range of flow rate values,
      lower the upper limit of the range of flow rate values when the first instruction is an instruction to lower the upper limit of the range of flow rate values,
      when receiving the second instruction, perform a comparison of the first transmission and reception time for the scanning line with the second transmission and reception time for the scanning line, the first transmission and reception time being based on scan conditions other than the range of flow rate values changed by the first instruction, and
      perform, based on a result of the comparison, an adjustment of at least one parameter included in the scan conditions for maintaining the range of flow rate values having the upper limit lowered by the first instruction, even if the second instruction is an instruction to increase the range of flow rate values.

7. The ultrasound diagnosis apparatus according to claim 6, wherein
the Doppler processing circuitry collects the blood flow information in a predetermined region of interest, and
the processing circuitry receives, as the second instruction, an instruction to change a setting related to the predetermined region of interest.

* * * * *